United States Patent [19]

Matsumoto et al.

[11] 4,215,077
[45] Jul. 29, 1980

[54] HYDROFORMYLATION OF OLEFINS

[75] Inventors: Mitsuo Matsumoto; Masuhiko Tamura, both of Kurashiki, Japan

[73] Assignee: Kuraray Co., Ltd., Kurashiki, Japan

[21] Appl. No.: 7,660

[22] Filed: Jan. 29, 1979

[30] Foreign Application Priority Data

Feb. 9, 1978 [JP] Japan ................................ 53/14410
Apr. 14, 1978 [JP] Japan ................................ 53/44611

[51] Int. Cl.$^2$ ............................................. C07C 45/10
[52] U.S. Cl. .................................. 568/454; 568/496; 568/862
[58] Field of Search .................. 260/604 HF; 568/909

[56] References Cited

U.S. PATENT DOCUMENTS

| 3,555,098 | 1/1971 | Olivier et al. | 260/604 HF |
| 3,576,881 | 4/1971 | Senn | 260/604 HF |
| 4,148,830 | 4/1979 | Pruett et al. | 260/604 HF |
| 4,152,344 | 5/1979 | Unruh | 260/604 HF |

FOREIGN PATENT DOCUMENTS

| 2715685 | 3/1977 | Fed. Rep. of Germany | 260/604 HF |
| 2730527 | 1/1978 | Fed. Rep. of Germany | 260/604 HF |
| 1338237 | 11/1973 | United Kingdom | 260/604 HF |

OTHER PUBLICATIONS

Jour. of Molecular Catalysis, vol. 3, pp. 101–109 (1977/1978) and vol. 3, 221–226 (1978).

Primary Examiner—Werren B. Lone
Attorney, Agent, or Firm—Barry Kramer

[57] ABSTRACT

Hydroformylation of olefins is effected in an organic solvent in the presence of a rhodium complex and a trisubstituted phosphine to give the corresponding aldehydes. Addition of a diphosphinoalkane of the general formula

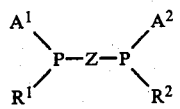

wherein, in the formula, A$^1$ and A$^2$ are each aryl, R$^1$ and R$^2$ are each aryl or saturated hydrocarbon residues containing one or more carbon atoms, and Z is an alkylene radical whose principal chain contains 2 to 5 carbon atoms and optionally may have one or more lower alkyl substituents, to the hydroformylation reaction system in an amount of 0.20 to 2.5 equivalents per gram atom of the rhodium contained in the rhodium complex markedly prolongs the life of the rhodium catalyst.

18 Claims, No Drawings

HYDROFORMYLATION OF OLEFINS

BACKGROUND OF THE INVENTION

1. Field of the Invention

This invention relates to a hydroformylation process. More particularly, it relates to an improved and advantageous process for producing aldehydes by hydroformylation of a lower olefin in an organic solvent in the presence of a rhodium complex and a trisubstituted phosphine, which comprises adding to the reaction system a diphosphinoalkane of the general formula

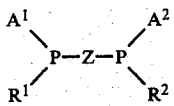 (I)

in an amount of 0.20 to 2.5 equivalents per gram atom of the rhodium present in said rhodium complex, wherein, in the formula, $A^1$ and $A^2$ are each aryl, $R^1$ and $R^2$ are each aryl or saturated hydrocarbon residues containing one or more carbon atoms, and Z is an alkylene radical whose principal chain contains 2 to 5 carbon atoms which optionally may be further substituted with one or more lower alkyls, whereby the catalyst life is markedly prolonged.

2. Description of the Prior Art

The hydroformylation reaction comprising reacting a lower olefin, typically ethylene, propylene or butene, with a hydrogen-carbon monoxide mixture in an organic solvent in the presence of a rhodium complex and a trisubstituted phosphine is well known and is being utilized, for instance, in the commercial production of butyraldehyde from propylene.

Rhodium complexes as hydroformylation catalysts have several advantages over cobalt catalysts. For example, the rhodium complexes can effect the reaction under much milder conditions (lower temperature, lower pressure) and bring higher selectivity toward normal aldehydes, and therefore are more suited for use in commercial production. However, the rhodium complexes are very expensive. Therefore, from an economic point of view, the value of said complexes as catalysts in commercial hydroformylation processes is very dependent on the life thereof. A number of attempts have so far been made to maintain the catalytic activity of the rhodium catalysts under the hydroformylation conditions for a prolonged period of time, leading to various proposals, which can be classified roughly into the following three categories:

(1) Inhibition of thermal degradation of the rhodium complexes under the reaction conditions and of formation of inactive, highly-carbonylated rhodium complexes by carrying out the reaction while keeping such reaction conditions as rhodium catalyst concentration, trisubstituted phosphine concentration, carbon monoxide partial pressure and reaction temperature each within a very limited or narrow range [see, for example, German patent application No. (abbreviated as DTOS) 2,715,685];

(2) Hydroformylation in the presence of a trace amount of oxygen in the reaction system (see, for example, DTOS No. 2,730,527); and (3) Hydroformylation while controlling the concentration in the reaction system of high boiling byproducts, which can serve as catalyst poisons below a specific level (see, for example, British Pat. No. 1,338,237 and DTOS No. 2,721,792).

There is, however, still room for improvement in practicing these processes. Thus, in case the measure described in (1) above is taken, the lowered reaction temperature and the increased trisubstituted phosphine concentration cause reduction of the reaction velocity, whereby it is required to use the expensive rhodium catalyst at a higher concentration so as to compensate for said reduction; accordingly measure (1) is considered disadvantageous from an economic point of view. Regarding the method (2) above, the trisubstituted phosphines and the product aldehydes are not stable against oxygen but may be converted into trisubstituted phosphine oxides and organic carboxylic acids, respectively, and as a result not only the catalytic is reduced, but also the product aldehydes are subjected to undesirable secondary reactions. The controlling of the concentration of high boiling byproducts below a certain level according to the method (3) above includes in industrial practice, frequent regeneration, activation and recovery of the rhodium catalyst which are accompanied by losses of the rhodium catalyst and the tri-substituted phosphine. Even when such measures as mentioned above are taken, decrease in the catalytic activity is still frequent during the reaction, making it unavoidable to regenerate, activate and recover the rhodium catalyst repeatedly. The procedure is complicated thereby to that extent, and losses of the rhodium catalyst and the trisubstituted phosphine result especially in the regeneration step. Because of these and other problems, the known methods of maintaining the activity of the rhodium catalyst remain to be further improved.

DETAILED DESCRIPTION OF THE INVENTION

It has now been found that the above problems can be solved in accordance with the present invention by adding to the reaction system for hydroformylation of a lower olefin, a diphosphinoalkane represented by the general formula

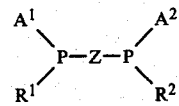 (I)

in an amount of 0.20 to 2.5 equivalents per gram atom of the rhodium contained in the rhodium complex, wherein, in the formula, $A^1$ and $A^2$ are each aryl, $R^1$ and $R^2$ are each aryl or a saturated hydrocarbon residue containing one or more carbon atoms, and Z is lower-alkyl-substituted or unsubstituted alkylene radical whose principal chain contains 2 to 5 carbon atoms. The present invention makes it possible to prolong the catalyst life of the rhodium catalyst markedly, to reduce the concentration of the trisubstituted phosphine to a level far below the concentration range heretofore employed, and as a result to increase the reaction velocity even at a lower temperature without the necessity of raising the rhodium catalyst concentration. Moreover, the possibility of carrying out the reaction at lower temperatures leads to the possibility of inhibiting the formation of undesirable high boiling byproducts, and consequently the catalytic activity can be stabilized and retained for a longer period of time. At the same time, the possible losses of the rhodium and the trisubstituted phosphine can be minimized owing to the resulting reduction in frequency of regeneration (recovery) procedures.

In the Journal of Molecular Catalysis 3, 101-109 (1977/78) and ibid. 3, 221-226 (1978), it is mentioned that hydroformylation in the presence of a diphosphinoalkane [e.g. 1,2-bis(diphenylphosphino)ethane] added to the rhodium catalyst gives satisfactory results in respect of reaction rate and selectivity (ratio of normal aldehydes to branched aldehydes) without any use of a trisubstituted phosphine such as triphenylphosphine or ethyldiphenylphosphine. However, the specific feature of this invention, namely the effect of prolonging the catalyst life, can be attained only when the trisubstituted phosphine is combined with a specific diphosphinoalkane in an amount within a very limited range. The present invention differs from the above-mentioned prior art literature in that the present invention employs a combination of the trisubstituted phosphine and the diphosphinoalkane. In case a combined system of the rhodium catalyst and the diphosphinoalkane alone is used for the reaction, the lowering of the catalytic activity is very rapid and remarkable, and the selectivity to normal aldehydes is not always satisfactory (cf. Example for Comparison -7 to be described hereinbelow).

The diphosphinoalkanes to be used according to the invention are represented by the general formula (I). The aryl groups represented by $A^1$ and $A^2$ and the aryl groups represented by $R^1$ and $R^2$ are each exemplified by phenyl and lower-alkyl-substituted phenyl, such as tolyl and xylyl. The saturated hydrocarbon residues represented by $R^1$ and $R^2$ are typically methyl, ethyl, propyl, butyl, pentyl, hexyl, heptyl, octyl, cyclohexyl, and the like. The alkylene radicals represented by Z can be, for example:

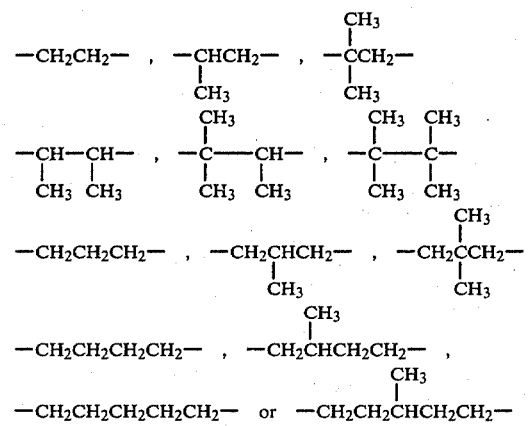

Mention can be made of the following as preferred examples of said diphosphinoalkanes:

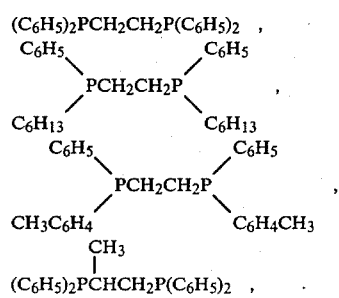

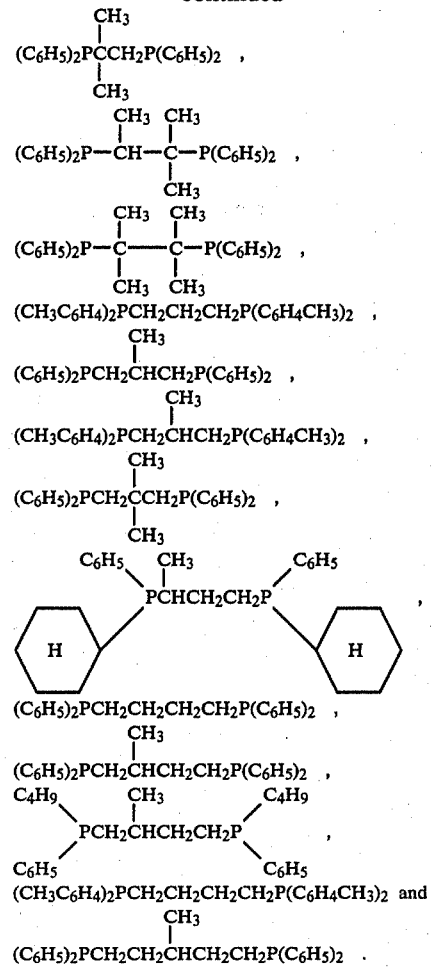

Among said diphosphinoalkanes, the following are preferred from the view point of availability, catalyst life prolonging effect and chemical stability, for instance.

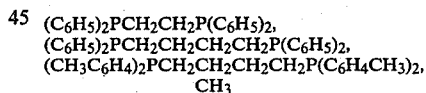

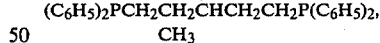

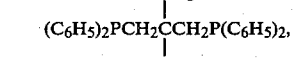

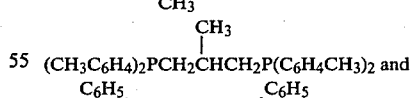

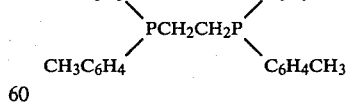

The above-mentioned diphosphinoalkanes can be used either singly or in combination. The amount of the diphosphinoalkane of formula (I) employed ranges between about 0.20 and 2.5 equivalents, and preferably ranges between about 0.25 and 2.0 equivalents, per gram atom of rhodium contained in the rhodium complex. When the amount of diphosphinoalkane does not reach 0.20 equivalent per gram atom of rhodium no substantial effect of the addition can be obtained. When, on the other hand, more than about 2.5 equivalents per rhodium atom of the diphosphinoalkane is used, the catalytic activity unfavorably decreases. It is preferable in industrial practice to carry out the hydroformylation of lower olefins by a continuous process. It is also preferable to carry out the reaction while supplementing the diphosphinoalkane either continuously or intermittently so as to maintain the concentration of the diphosphinoalkane in the reaction system approximately at a predetermined level.

In accordance with this invention, it is essential to employ an excess of the trisubstituted phosphine with respect to the rhodium complex, in addition to said diphosphinoalkane. The addition of the trisubstituted phosphine has beneficial effects on the selectivity of the reaction (particularly that to the normal aldehyde) and the catalyst life. The proportion of said trisubstituted phosphine based on the rhodium complex is 10 to 500 equivalents per rhodium atom in the complex and, for better results, 25 to 300 equivalents on the same basis. There are many different trisubstituted phosphines to choose from, although triarylphosphines, triaryl phosphites, alkyldiarylphosphines, and particularly, triphenylphosphine, trinaphthylphosphine, tritolyphosphine, triphenyl phosphite and propyldiphenylphosphine are desirable in consideration of availability, catalyst activity, reaction selectivity and catalyst life.

This invention can be practiced by employing an optional rhodium complex having an activity to catalyze hydroformylation. While a number of such rhodium complexes are known, those rhodium complexes having the general formula: $HRh(CO)(PR_3)_3$ (where R is alkyl or aryl) or of the so-called rhodium carbonyl cluster type are preferred from the standpoint of catalyst activity, solubility, ease of use and other properties. As typical examples of such rhodium complexes, there may be mentioned the compounds having one of the formulas: $HRh(CO)[P(C_6H_5)_3]_3$, $HRh(CO)[P(C_6H_4CH_3)]_3$, $Rh_4(CO)_{12}$ and $Rh_6(CO)_{16}$. It is also feasible to provide a separate vessel for preparing the catalyst so that the rhodium complex may be prepared therein and the resultant reaction mixture be directly fed to the reactor for the contemplated hydroformylation reaction.

In the practice of this invention, the rhodium complex is employed in such an amount that its concentration within the reaction system ranges from about 0.1 to 25 mg. atoms/liter as rhodium metal. If the concentration of the rhodium complex is less than about 0.1 mg. atom/liter, the reaction rate will not be as high as might be desired. Conversely, if the concentration is above about 25 mg. atoms/liter, the economics of the process will be sacrificed due to the high cost of the rhodium compound; also, a further disadvantage of a decreased catalyst life is noted.

The method of this invention is applicable with particular advantage to lower olefins containing 2 to 5 carbon atoms. As examples of such lower olefins, there may be mentioned ethylene, propylene, 1-butene, isobutene, 1-pentene, allyl alcohol, allyl methyl ether, and the like.

There is no special limitation on the type of organic solvent used, except that it be able to dissolve the rhodium complex, trisubstituted phosphine and diphosphinoalkane and does not interfere with the hydroformylation reaction. Commercially speaking, it is desirable cost-wise to employ the product aldehyde and its condensation by product as the main reaction solvent. Aside from such solvents, there may be mentioned aromatic hydrocarbons such as benzene, toluene, xylene, dodecylbenzene; alicyclic hydrocarbons such as cyclohexane; ethers, ketones, esters, and the like.

The contemplated hydroformylation reaction is carried out by feeding carbon monoxide gas and hydrogen gas into such organic solvents containing said rhodium complex, trisubstituted phosphine, diphosphinoalkane and lower olefin. The reaction temperature is a critical reaction parameter in that it is determinant of the reaction rate and catalyst life, and is desirably within the range of room temperature to 130° C. and, for still better results, 40° to 110° C. It is not practically advisable to conduct the reaction at temperatures below room temperature, nor is it desirable to carry out the reaction at temperatures over about 130° C. for the catalyst activity would not then be sustained and, hence, the desired object would not be attained.

The partial pressure ratio of hydrogen to carbon monoxide is preferably within the range of 1:2 to 5:1 as the feed mixed gas and it is important from such considerations as reaction rate, selectivity and catalyst life that the absolute partial pressure of carbon monoxide in the reaction system be within the range of 0.1 to 2.5 atms. during the progress of the reaction. When the absolute partial pressure of carbon monoxide is in excess of about 2.5 atms., the relative amount of side-chain type aldehyde is increased and the catalyst life is shortened. When use is made of a lower olefin which is gaseous at atmospheric temperature and pressure, it is commercially advantageous to ensure that the total pressure of olefin, hydrogen and carbon monoxide be within the range of 5 to 30 atms.

The reaction system may contain such impurity gases inert to the hydroformylation reaction, as nitrogen, helium, argon, methane, ethane, propane and butane.

For commercial runs, the hydroformylation reaction is desirably carried out by a continuous method employing a stirring-type reaction vessel or a columnar reaction vessel. When the product aldehyde is comparatively low-boiling, it can be taken out from the reaction system predominantly along with the off-gas, thus facilitating reuse of the catalyst components, too. Conversely, when the product aldehyde is high-boiling, the dissolved gas is first released by decompression or depressurization and, then, the product is separated by distillation. In the latter case, i.e. distillation, it is advisable for the maintenance of catalyst life to conduct the distillation at a suitable degree of reduced pressure so that the temperature of the liquid phase will be as low as possible. The residue consisting of product aldehyde, catalyst components and minor amounts of high-boiling byproducts is recycled to the hydroformylation stage.

When the product aldehyde is a thermally unstable substance such as hydroxybutyraldehyde from allyl alcohol, it is advantageous to separate the product by a method other than distillation, e.g. extraction with a solvent. As far as hydroxybutyraldehyde is concerned, a desirable procedure can comprise extracting the product from the reaction mixture by means of water and recycling the extraction residue containing the catalyst components (organic solution) to the hydroformylation reaction stage. It may be desirable, if necessary, to subject a small portion of said extraction residue to a catalyst activation treatment. For commercial purposes, the quantity of water used for the aqueous extraction of hydroxybutyraldehyde is desirably within the range of 0.5 to 1.5 by volume based on the hydroformylation reaction mixture. The water for this purpose may contain other substances within amounts which will not interfere with the process and product. The most common of such substances are 2-methyl-1,3-propanediol and/or 1,4-butanediol and the water may be replaced with these materials in a proportion of up to 50%.

For this aqueous extraction of the product and catalyst components, the organic solvent for the hydroformylation reaction must be an organic solvent capable of dissolving the rhodium complex and trisubstituted phosphine and sparingly miscible with water. Thus, aromatic hydrocarbons such as benzene, toluene, xylene, and the like and alicyclic hydrocarbons such as cyclohexane, and the like are particularly useful.

The examples given hereinafter are illustrative of this invention. It should be understood that, in Examples 1 through 7 and Examples for Comparison 1 through 7, the reaction was invariably carried out in a 1-liter stainless steel autoclave fitted with a magnetic stirrer, thermometer, gas inlet and gas outlet. "Ph" means phenyl.

EXAMPLE 1

The autoclave was charged with a solution of 0.60 millimole of HRh(CO)(PPh$_3$)$_3$, 40 millimoles of triphenylphosphine and 0.30 millimole of 1,2-bis(diphenylphosphino) ethane in 150 ml of n-butyraldehyde plus 250 ml of dioctyl phthalate. The system was purged first with nitrogen and then with a mixture of hydrogen and carbon monoxide (molar ratio=2:1). While maintaining the temperature within the reaction vessel at 85° C., propylene, carbon monoxide, hydrogen and nitrogen were fed into the autoclave through the gas inlet at rates of flow of 30, 20, 40 and 140 liters per hour, respectively. The reaction gas containing the butyraldehydes (isobutyraldehyde and n-butyraldehyde) that had formed was continuously discharged under control by means of a pressure-adjusting valve disposed in the course of the gas outlet tube so as to keep a pressure of 15 kg/cm$^2$ (absolute pressure) within the autoclave. It was confirmed by means of a level gauge that the level of liquid contents of the autoclave remained constant after a steady state had been reached. The butyraldehydes that had formed were trapped by bubbling the emerging gas in toluene cooled with dry ice and acetone. Each fraction of the aldehydes collected for a certain definite period of time was analyzed by gas chromatography. The emerging gas was also analyzed by gas chromatography for carbon monoxide, hydrogen, propylene and propane.

The carbon monoxide content of the emerging gas after 20 hours of reaction was 2.8%, and the rates of formation of n-butyraldehyde and isobutyraldehyde were 0.583 and 0.056 moles/hour, respectively.

The rates of formation of the total butyraldehydes consisting of n-butyraldehyde and isobutyraldehyde after 20 hours and 170 hours are shown in Table 1. The fact that the formation rate for the butyraldehydes after 170 hours revealed little decrease when compared with that after 20 hours shows that the catalytic activity was retained during the reaction period practically without decrease. The ratio of the formation rate for n-butyraldehyde to that for isobutyraldehyde after 170 hours of reaction was almost the same as the corresponding ratio after 20 hours.

EXAMPLES 2 to 4

The procedure of Example 1 was followed except that diphosphinoalkanes each specified in Table 1 were used in place of the 1,2-bis(diphenylphosphino)ethane. The butyraldehyde formation rates after 20 and 170 hours of reaction were as shown in Table 1. No substantial decrease in the formation rate was found. The ratio of the n-butyraldehyde formation rate to the isobutyraldehyde formation rate was almost the same as that obtained in Example 1.

Table 1

| Ex. | Disphosphino compound Kind | Added in amount (mole/gram atom Rh) | Rate of formation of butyraldehydes (mole/hour) after 20 hours | 170 hours |
|---|---|---|---|---|
| 1 | Ph$_2$P(CH$_2$)$_2$PPh$_2$ | 0.50 | 0.639 | 0.632 |
| 2 | Ph$_2$PCH$_2$CH(CH$_3$)CH$_2$P(-C$_6$H$_4$-CH$_3$)$_2$ | 0.75 | 0.635 | 0.617 |
| 3 | Ph$_2$PCH$_2$CH$_2$CH(CH$_3$)CH$_2$CH$_2$PPh$_2$ | 1.0 | 0.653 | 0.618 |
| 4 | (CH$_3$-C$_6$H$_4$-)$_2$PCH$_2$CH$_2$P(-C$_6$H$_4$-CH$_3$)$_2$ | 0.60 | 0.618 | 0.613 |

EXAMPLE 5

A solution of 0.15 mmole of Rh$_6$(CO)$_{16}$, 60 mmoles of tritolylphosphine and 0.60 mmole of 1,4-bis(diphenylphosphino) butane in 100 ml of propionaldehyde plus 300 ml of dioctyl phthalate was used as catalyst solution. The temperature within the autoclave was maintained at 70° C. Ethylene, carbon monoxide, hydrogen and nitrogen were introduced at rates of flow of 45, 30, 60 and 85 liters per hour, respectively. While maintaining the pressure within the autoclave at 13 kg/cm$^2$ (absolute pressure), the reaction was effected by the procedure of Example 1. The rates of formation of propionaldehyde at 20 and 170 hours after commencement of the reaction were 1.01 moles and 0.990 mole per hour, respectively. Little decrease in the formation rate revealed that the catalyst activity had been well sustained.

EXAMPLE 6

The procedure of Example 5 was followed except that the catalyst components were 0.60 mmole of HRh(CO)(PPh$_3$)$_3$, 30 mmoles of triphenyl phosphite and 0.45 mmole of 1,5-bis(diphenylphosphino)pentane. The propionaldehyde formation rates after 20 and 170 hours were 0.893 and 0.854 mole per hours, respectively.

EXAMPLE 7

A solution of 0.60 mmole of HRh(CO)[P(tolyl)$_3$]$_3$, 90 mmoles of triphenylphosphine and 0.45 mmole of 1,2-bis (diphenylphosphino)ethane in 200 ml of pentanal plus 200 ml of dioctyl phthalate was used as catalyst solution, and the temperature within the autoclave was kept at 105° C. 1- Butene, carbon monoxide, hydrogen and nitrogen were introduced at rates of 30, 20, 40 and 140 liters per hours. The reaction was carried out according to the procedure of Example 1, while maintaining the pressure at 13 kg/cm² (absolute pressure). The rates of formation of pentanals after 20 and 170 hours of reaction were found to be 0.719 and 0.690 mole per hour, respectively.

In the following Examples 8 to 15, the reaction was carried out in a 300-ml glass autoclave equipped with thermometer, magnetic stirrer, reflux condenser, gas inlet and gas outlet.

EXAMPLE 8

The autoclave was charged with a solution of 0.10 mmole of $HRh(CO)(PPh_3)_3$, 7.5 mmoles of triphenylphosphine and 0.075 mmole of 1,4-bis(diphenylphosphino)butane in 80ml of toluene and 20.0 g of allyl alcohol. The autoclave was purged first with nitrogen gas and then with a mixture of hydrogen and carbon monoxide (molar ratio=2:1), then immersed in a water bath and heated so that the temperature within it was kept at 65° C. A mixed gas consisting of hydrogen and carbon monoxide in a molar ratio of 2:1 was then introduced. The pressure within the autoclave was maintained at 3.0 kg/cm² (absolute) and the rate of flow of the emerging gas at 20 Nl/hr. At the time when these conditions were attained, stirring was begun (this time point was considered as the time when the reaction began to proceed). The emerging gas was passed through a toluene trap cooled with dry ice and acetone in order to collect the accompanying allyl alcohol, propionaldehyde and other products. The hydroformylation of allyl alcohol was continued in this manner at constant pressure and constant temperature for 2.0 hours. The conversion of allyl alcohol after 2.0 hours of reaction was found to be more than 95% by gas chromatography of the reaction product and of the liquid within the toluene trap. The yields of propionaldehyde and n-propanol were 22.9 and 9.8 mmoles, respectively. After discontinuation of the reaction, the liquid reaction mixture was cooled to room temperature, depressurized, transferred carefully in an atmosphere consisting of hydrogen and carbon monoxide (molar ratio=2:1) into a 300-ml separating funnel, and extracted with two 50-ml portions of distilled water carefully in the same atmosphere so as to separate hydroxybutyraldehydes contained in the reaction mixture. (It was established by a separate experiment that more than 95% of the hydroxybutyraldehydes existing in the reaction mixture could be extracted into the aqueous layer by said extraction procedure). The organic layer (toluene solution containing the catalyst components) was charged together with 20.0 g of fresh allyl alcohol into the autoclave, the hydroformylation reaction was carried out for 2 additional hours by the above procedure, and the resulting hydroxybutyraldehydes were extracted with water by the above procedure. The above hydroformylation reaction of allyl alcohol followed by the water extraction of hydroxybutyraldehydes was repeated ten times in all. The analysis for hydroxybutyraldehydes was carried out after these were converted into the corresponding glycols by hydrogenation, because of thermal unstableness of hydroxybutyraldehydes which made it impossible to gas-chromatograph the same as they were. Thus, the aqueous layers (extract solutions containing hydroxybutyraldehydes) obtained by the extraction of run numbers 1 to 3, run numbers 4 to 6, and run numbers 8 to 10 combined respectively. Each of the resulting three portions amounted to about 350 ml. A one-liter autoclave was charged with each said portion together with 10.0 g of Raney nickel, and hydrogenation was carried out at a temperature of 60° C. and a hydrogen pressure of 50 kg/cm² (absolute) for 5 hours. The hydroxybutyraldehydes were converted by this hydrogenation into 1,4-butanediol (hereinafter 1,4-BD) and 2-methyl-1,3-propanediol (hereinafter MPD). The 1,4-BD and MPD were determined by gas chromatography.

It was separately confirmed by a blank experiment and from the mass balance that the hydrogenation of said extract solution could convert hydroxybutyraldehydes almost quantitatively into the corresponding glycols.

The total amounts of 1,4-BD and MPD produced in this manner by the hydroformylation of allyl alcohol followed by the hydrogenation of the resulting aldehydes are shown in Table 2 for runs 1 to 3, 4 to 6 and 8 to 10.

EXAMPLES 9 TO 14

The hydroformylation of allyl alcohol followed by extraction with water was repeated ten times in all according to the procedure of Example 8, except that the diphosphinoalkane, trisubstituted phosphine and solvent used were those specified in Table 2. The results obtained after the hydrogenation of the extracts by the procedure of Example 8 are shown in Table 2.

Table 2

| Ex. | Trisubstituted phosphine (mmoles) | Diphosphino compound (mole(s)/ gram atom Rh) | | Solvent | Yields of butanediols (mmoles) | | | | | |
|---|---|---|---|---|---|---|---|---|---|---|
| | | | | | Runs[1-3] | | Runs[1-6] | | Runs[8-10] | |
| | | | | | 1,4-BD | MPD | 1,4-BD | MPD | 1,4-BD | MPD |
| 8 | PPh₃ (7.5) | Ph₂P(CH₂)₄PPh₂ | (0.75) | Toluene | 765 | 117 | 768 | 118 | 766 | 120 |
| 9 | PPh₃ (5.0) | Ph₂P(CH₂)₄PPh₂ | (1.0) | Benzene | 768 | 116 | 761 | 120 | 765 | 118 |
| 10 | PPh₃ (5.0) | ((C₆H₄)₂-PCH₂CH₂P-(C₆H₄)₂)₂ with CH₃ substituents | (0.75) | Toluene | 765 | 117 | 769 | 119 | 754 | 120 |
| 11 | P-(C₆H₄-CH₃)₃ (7.5) | Ph₂P(CH₂)₃PPh₂ | (0.75) | Benzene | 762 | 120 | 768 | 117 | 760 | 114 |

Table 2-continued

| Ex. | Trisubstituted phosphine (mmoles) | | Diphosphino compound (mole(s)/ gram atom Rh) | | Solvent | Yields of butanediols (mmoles) | | | | | |
|---|---|---|---|---|---|---|---|---|---|---|---|
| | | | | | | Runs 1-3 | | Runs 1-6 | | Runs 8-10 | |
| | | | | | | 1,4-BD | MPD | 1,4-BD | MPD | 1,4-BD | MPD |
| 12 | P–(–⟨CH₃⟩–)₃ with CH₃ | (7.5) | Ph₂PCH₂CHCH₂P–(–⟨CH₃⟩–)₂  | (0.65) | Cyclohexane | 765 | 122 | 769 | 123 | 767 | 121 |
| 13 | PPh₃ | (7.5) | Ph\CH₃/Ph<br>PCH₂CCH₂P<br>/C₈H₁₇  CH₃  \C₈H₁₇ | (0.5) | Toluene | 759 | 118 | 757 | 117 | 755 | 117 |
| 14 | PPh₃ | (5.0) | CH₃<br>\|<br>Ph₂PCH₂CH₂CHCH₂CH₂PPh₂ | (1.25) | Toluene | 763 | 121 | 762 | 120 | 765 | 122 |

EXAMPLE 15

Following the procedure of Example 8, the hydroformylation of allyl alcohol was carried out, except that, in the first run, the amount of triphenylphosphine was 7.5 mmoles and the amount of 1,4-bis(diphenylphosphino)-butane was 0.025 mmoles (the remaining conditions were the same as those employed in Example 8), and that, in each of the second and the following runs, 20.0 g of allyl alcohol was charged together with 0.006 mmole of fresh 1,4-bis(diphenylphosphino) butane. Twenty runs were carried out in total. The total yields of 1,4-BD and MPD for runs 1 to 3 were 767 and 110 mmoles, respectively, while the total yields of 1,4-BD and MPD for runs 18 to 20 were 753 and 116 mmoles, respectively.

EXAMPLE FOR COMPARISON-1

The procedure of Example 1 was followed except that 1,2-bis(diphenylphosphino)ethane was not used.

The rates of formation of butyraldehydes after 20 and 170 hours were as shown in Table 3, revealing a very remarkable decrease in the formation rate in the course of time, as compared with the results obtained in Example 1. The ratio of the n-butyraldehyde formation rate to the isobutyraldehyde formation rate was not very different from that obtained in Example 1.

EXAMPLES FOR COMPARISON-2 TO 6

The procedure of Example 1 was followed except that the diphosphinoalkanes identified in Table 3 were used in place of 1,2-bis(diphenylphosphino)ethane. The formation rates for butyraldehydes after 20 and 170 hours of reaction were as shown in Table 3.

Table 3

| Example for Comparison | Diphosphino compound | | Rate of formation of butyraldehyde (mole/hour) | |
|---|---|---|---|---|
| | Kind | Added in amount (mole(s)/gram atom Rh) | | |
| 1 | — | — | 0.698 | 0.521 |
| 2 | Ph₂P(CH₂)₂PPH₂ | 5.0 | 0.084 | 0.072 |
| 3 | Ph₂P(CH₂)₄PPh₂ | 0.10 | 0.691 | 0.529 |
| 4 | Ph₂PCH₂PPh₂ | 0.75 | 0.605 | 0.423 |
| 5 | Ph₂P(CH₂)₆PPh₂ | 1.0 | 0.620 | 0.329 |
| 6 | Ph₂PCH₂CH=CHCH₂PPh₂ | 1.0 | 0.641 | 0.454 |

EXAMPLE FOR COMPARISON-7

The procedure of Example 1 was followed except that no triphenylphosphine was used. Analysis of the emerging gas immediately after commencement of the reaction for carbon monoxide and propylene concentrations revealed that the reaction had been very rapid at that time point. However, the lowering of catalytic activity was so intense that the rate of formation of butyraldehydes after 20 hours of reaction amounted only to 0.097 mole/hr. The ratio of the n-butyraldehyde formation rate to the isobutyraldehyde formation rate was 3:5:1, the proportion of isobutyraldehyde being greater than that found in Example 1.

What is claimed is:

1. In a process for producing aldehydes by hydroformylating a lower olefin which comprises ethylene, propylene, 1-butene, isobutene, 1-pentene, allyl alcohol or allyl methyl ether at a temperature within the range of from about room temperature to 130° C., in an organic solvent in the presence of a rhodium complex having the general formula $$HRh(CO)(PR_3)_3$$

wherein R is alkyl or aryl, or a rhodium carbonyl cluster, employed at a concentration of from 0.1 to 25 mg atoms/l of reaction mixture, and a trisubstituted phosphine in an amount of from 10 to 500 equivalents per rhodium atom, while maintaining a carbon monoxide partial pressure within the range of 0.1 to 2.5 atmospheres during the progress of the reaction and a ratio of hydrogen partial pressure to that of the carbon monoxide within the range of 1:2 to 5:1, the improvement which comprises adding to the reaction system a diphosphino alkane represented by the general formula

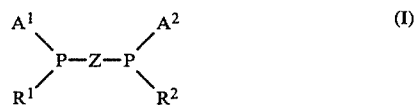

(I)

in an amount of 0.20 to 2.5 equivalents per gram atom of the rhodium present in said rhodium complex, wherein, in the formula, $A^1$ and $A^2$ are each aryl, $R^1$ and $R^2$ are each aryl or a saturated hydrocarbon residue containing one or more carbon atoms, the aryl groups being selected from the group consisting of unsubstituted phenyl and napthyl groups and phenyl and napthyl groups substituted with lower alkyl groups, and Z is an alkylene radical whose principal chain contains 2 to 5 carbon atoms, said alkylene radical being selected from the group consisting of unsubstituted alkylenes and alkylenes substituted with at least one lower alkyl radical.

2. A hydroformylation process as claimed in claim 1, wherein the concentration of said rhodium complex in the reaction system is, when expressed in terms of the rhodium present, 0.1 to 25 milligram atoms per liter.

3. A hydroformylation process as claimed in claim 1, wherein said rhodium complex is HRh(CO)[P(C$_6$H$_5$)$_3$]$_3$, HRh(CO)[P(C$_6$H$_4$CH$_3$)$_3$]$_3$, Rh$_4$(CO)$_{12}$ or
Rh$_6$(CO)$_{16}$.

4. A hydroformylation process as claimed in claim 1, wherein said trisubstituted phosphine is selected from the group consisting of triarylphosphines, triarylphosphites and alkyldiarylphosphines.

5. A hydroformylation process as claimed in claim 4, wherein said trisubstituted phosphine is triphenylphosphine, trinaphthylphosphine, tritolylphosphine, triphenylphosphite or propyldiphenylphosphine.

6. A hydroformylation process as claimed in claim 1, wherein said trisubstituted phosphine is used in an amount of 10 to 500 equivalents per gram atom of the rhodium contained in said rhodium complex.

7. A hydroformylation process as claimed in claim 6, wherein said trisubstituted phosphine is used in an amount of 25 to 300 equivalents per gram atom of the rhodium contained in said rhodium complex.

8. A hydroformylation process as claimed in claim 1, wherein said diphosphinoalkane is

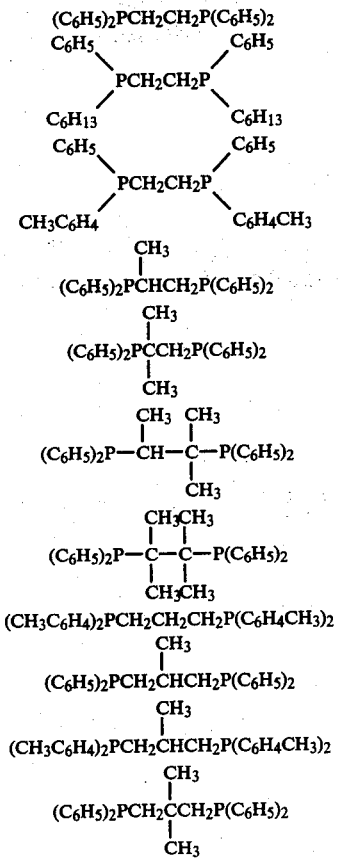

9. A hydroformylation process as claimed in claim 8, wherein said diphosphinoalkane is a diarylphosphinoalkane.

10. A hydroformylation process as claimed in claim 11, wherein said diphosphinoalkane is

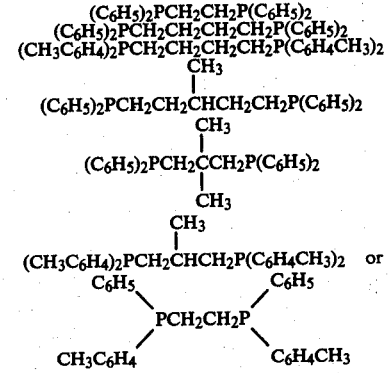

11. A hydroformylation process as claimed in claim 1, wherein said diphosphinoalkane is added to the reaction system in an amount of 0.25 to 2.0 equivalents per gram atom of the rhodium contained in said rhodium complex.

12. A hydroformylation process as claimed in claim 1, wherein the reaction temperature is in the range of 40° C. to 110° C.

13. A hydroformylation process as claimed in claim 1, wherein the ratio of the partial pressure of hydrogen to that of carbon monoxide as determined for the feed gases is in the range between 1:2 and 5:1.

14. A hydroformylation process as claimed in claim 13, wherein the partial pressure of carbon monoxide in the reaction system is 0.1 to 2.5 atmospheres (absolute pressure).

15. A hydroformylation process as claimed in claim 1, wherein the reaction is carried out in the presence of an organic solvent.

16. A hydroformylation process as claimed in claim 15, wherein the lower olefin is ethylene, propylene, 1-butene, isobutene or 1-pentene and said organic solvent is the product aldehyde or a condensation product thereof, an aromatic or alicyclic hydrocarbon, an ether, a ketone or an ester.

17. A hydroformylation process as claimed in claim 15, wherein the lower olefin is allyl alcohol and said organic solvent is an aromatic or alicyclic hydrocarbon.

18. A hydroformylation process as claimed in claim 1, wherein said lower olefin is allyl alcohol, and wherein the reaction product is extracted with water from the reaction mixture and the residual solution is recycled to the hydroformylation reaction system in the form of a catalyst solution.

* * * * *

UNITED STATES PATENT AND TRADEMARK OFFICE
CERTIFICATE OF CORRECTION

PATENT NO. : 4,215,077
DATED : July 29, 1980
INVENTOR(S) : M. Matsumoto et al

It is certified that error appears in the above—identified patent and that said Letters Patent is hereby corrected as shown below:

In Claim 10, line 2, "11" should read --9--.

Signed and Sealed this

Eleventh Day of November 1980

[SEAL]

Attest:

SIDNEY A. DIAMOND

*Attesting Officer*     *Commissioner of Patents and Trademarks*